(12) United States Patent
Wehrli

(10) Patent No.: US 6,475,471 B1  
(45) Date of Patent: *Nov. 5, 2002

(54) SYSTEM AND METHOD FOR APPLYING ORAL FLUID ABSORBING MATERIAL TO DENTAL ARCHES, WITH APPLICATION IN TREATMENT OF PERIODONTAL GUM DISEASE

(76) Inventor: Janet M. Wehrli, 6737 S. 153 Cir., Omaha, NE (US) 68137

( * ) Notice: Subject to any disclaimer, the term of this patent is extended or adjusted under 35 U.S.C. 154(b) by 0 days.

This patent is subject to a terminal disclaimer.

(21) Appl. No.: 10/008,929

(22) Filed: Nov. 3, 2001

Related U.S. Application Data

(63) Continuation-in-part of application No. 09/549,301, filed on Apr. 13, 2000, now Pat. No. 6,322,772
(60) Provisional application No. 60/145,028, filed on Jul. 22, 1999.

(51) Int. Cl.$^7$ .............................. A61K 7/16; A61K 5/00; A61K 5/14
(52) U.S. Cl. ........................... 424/49; 433/80; 433/215; 433/216
(58) Field of Search ....................... 424/49–58; 433/80, 433/215

(56) References Cited

U.S. PATENT DOCUMENTS

| | | | | |
|---|---|---|---|---|
| 3,339,547 A | * | 9/1967 | Drabkowski | 128/260 |
| 3,527,219 A | * | 9/1970 | Greenberg | 128/260 |
| 3,844,286 A | * | 10/1974 | Cowen | 128/260 |
| 4,344,931 A | * | 8/1982 | Aguilar | 424/49 |
| 4,812,308 A | * | 3/1989 | Winston et al. | 424/49 |
| 4,813,613 A | * | 3/1989 | Salete | 241/7 |
| 4,981,698 A | * | 1/1991 | Cherukuri et al. | 426/5 |
| 4,983,379 A | | 1/1991 | Schaeffer | 424/52 |
| 5,004,595 A | * | 4/1991 | Churukuri et al. | 424/49 |
| 5,038,396 A | * | 8/1991 | Gjerlov | 424/737 |
| 5,094,843 A | | 3/1992 | Mazzanobile et al. | 424/52 |
| 5,143,728 A | * | 9/1992 | Cappel et al. | 424/195.1 |
| 5,294,432 A | * | 3/1994 | Winston et al. | 424/49 |
| 5,323,787 A | * | 6/1994 | Pratt | 128/862 |
| 5,380,530 A | | 1/1995 | Hill | 424/440 |
| 5,385,727 A | | 1/1995 | Winston et al. | 424/49 |
| 5,445,826 A | * | 8/1995 | Kuhrtz | 424/451 |
| 5,455,024 A | | 10/1995 | Winston et al. | 424/52 |
| 5,466,469 A | * | 11/1995 | Kuhrtz | 424/451 |
| 5,575,654 A | * | 11/1996 | Fontenot | 433/215 |
| 5,632,972 A | | 5/1997 | Williams et al. | 424/49 |
| 5,695,745 A | | 12/1997 | Barton et al. | 424/49 |
| 5,846,570 A | | 12/1998 | Barrow et al. | 424/616 |
| 5,863,202 A | * | 1/1999 | Fontenot | 433/215 |
| 5,869,029 A | * | 2/1999 | Graff-Andersen et al. | 424/52 |
| 5,948,439 A | * | 9/1999 | Forman et al. | 424/466 |
| 6,086,856 A | * | 7/2000 | Saferstein et al. | 424/49 |
| 6,258,342 B1 | * | 7/2001 | Harcum et al. | 424/49 |
| 6,280,708 B1 | | 8/2001 | Ryles et al. | 424/53 |
| 6,322,772 B1 | * | 11/2001 | Wehrli | 424/49 |

FOREIGN PATENT DOCUMENTS

| | | | |
|---|---|---|---|
| JP | 2000044446 | * | 2/2000 |

OTHER PUBLICATIONS

Shibly, O, Ciancio, S, et al. Clinical Evaluation of the Effect of a Hydrogen Peroxide Mouth Rinse, Sodium Bicarbonate Dentifrice, and Mouth Moisturizer on Oral Health. J Clin Dent. vol. VIII (8). P. 145–149, 1997.

Slots, J., Rams, T.E. Local Delivery of Antimicrobial Agents in the Periodontal Pocket. Periodontology–2000, 1996 Feb.; 10: 139–159.

Hefferren, J.J. Historical view of Dentifrice Functionality Methods. J Clin Dent 1998 IX(3):53–56.

Mankodi, S., Berkowtiz, H. et al. Evaluation of the Effects of Brushing on the Removal of Dental Plaque. J Clin Dent 1998 IX (3):57–60.

Habib, C.M., Kugel, G., et al. Preliminary Report: Laboratory–induced Stain Removal as Assessed by Environmental Scanning Electron Microscopy. J. Clin Dent 1998 IX (3): 64–66.

Koertge, T.E., Brooks, C.N. et al. A Longitudinal Comparison of Tooth Whitening Resulting from Dentifrice Use. J. Clin Dent 1998 IX (3):67–71.

Kleber, C.J., Nelson, B.J., Laboratory Assessment of Tooth Whitening by sodium Bicarbonate Dentifrices. J Clin Dent 1998 IX (3): 72–75.

Academy of General Dentistry. Dental Health Fact Sheets: Gum Disease. http://www.agd.org/consumer/facts/gumdisease.html. 1999, Oct.

Drake, D.R., Vargas, K., et al. Enhance Bactericidal Activity of Arm and Hammer Dental Care. Am J Dent 1995 Dec: 8 (6); 308–312.

Barnes, C.M. An Evidence–Based Review of Sodium Bicarbonate as a Dentifrice Agent. Comp of Cont Ed in Oral Hygiene. 1997. 6(3);3–9.

John, C., Preventing Infective Endocarditis: A review of Current Practice Protocols. J Prac Dent Hyg 1999, Sep.–Oct.; 55–59.

The American Academy of Periodontology, Current Understanding of the Role of Microscopic Monitoring, Baking Soda and Hydrogen Peroxide in the Treatment of Periodontal Disease. Committee on Research, Science and Therapy, Apr. 1994.

Biological Therapies in Dentistry; A Bimonthly Newsletter for Dental Professionals. Vol. 13, Apr. 1997.

(List continued on next page.)

Primary Examiner—Shep K. Rose
(74) Attorney, Agent, or Firm—James D. Welch

(57) ABSTRACT

Disclosed is a method which provides for positioning materials which absorb oral fluids in into controlled, direct contact with at least one dental arch of a subject. The method is particularly applicable to treatment of periodontal gum disease where the material is made from a mixture of bicarbonate of soda, psyllium husk fiber and optionally at least one antimicrobial agent, in combination with a moistening agent and optional flavoring.

25 Claims, No Drawings

OTHER PUBLICATIONS

Van der Ouderaa F J G and Cummins D.,Delivery Stystems for Agents in Supra–and Sub–gingival Plaque Control. J Dent Res 1989, 68, 1617–1624.

Blake–Haskins, J.C., Gaffar, A., Volpe, A.R., The Effect of fBicarbonate/Fluoride Dentifrices on Human Plaque pH J Clin Dent 8: 173–177, 1997.

West, Theodore L., King, William J., Toothbrushing With Hydrogen Peroxide–Sodium Bicarbonate Compared to Toothpowder and Water in Reducing Periodontal Pocket Suppuration and Darkfield Bacterial Counts. J. Periodontology, Jun. 1983.

Rams, Thomas E., Keyes, Paul H., Wright, William E., Howard, Surya A., Long–term effects of microbiologically modulated periodontal therapy on advanced adult periodontitis. JADA, vol. 111, Sep. 1985.

Burnett, Larry, An introduction to subgingival ultrasonic scaling. Instructional information from Dentsply Internataional, Inc.

Katoh H. Incidence of transient bacteremia following dental surgery–prophylactic use of cefuroxime, ceftriaxone or clindamycin. Tokai J Exp Clin Med, 17(3.–4):109–13 1992 Oct. Medluie Identifier No. 93242620.

Carroll GC; Sebor RI. Dental flossing and its relationship to transient bacteremia. i Periodontol, 51(12):691–2 1980 De Medline Identifier No. 81144535.

Wank HA: Levison ME; Rose LF; Cohen DW. A quantitative measurement of bacterentia and its relationship to plaque control J Periodontol, 47(12):683–6 1976 Dec. Medline Identifier No. 77053355.

Baltch AL; Schaffer C; Hammer MC; Sutphen NT; Smith RP; Conroy J; Shayegani M. Bacteremia following dental cleaning patients with and without penicillin prophylaxis. Am Heart J, 104(6): 1335–9 1982 Dec. Medling Identifier No. 83071.

Rosling BG: Slots J; Webber RL: Christersson LA: Genco RJ, Microbiological and clinical effects of topical subgingival antimicrobial treatment on human periodontal disease. J Clin Periodontal, 1983 Sep., 10:5, 487–514.

Miyasaki KT; Genco RJ; Wilson ME, Antimicrobial properties of hydrogen peroxide and sodium bicarbonate individually and in combination against selected oral, gram–negative, facultative bacteria. J Dent Res, 1986 Sep., 65–9, 1142–8.

Lang WP, Farghaly MM, Ronis DL, The relation of preventive dental behaviors to periodontal health status. J Clin Periodontal 1994; 21: 194–198.

ThirdAge.com, http://www.thirdage.com/news/archive/980813–05.html?rs. Floss Away to Avoid Gum Woes. Archive Aug. 13, 1998.

ThirdAge.com, http://www.thirdage.com/news/archive/980915–03.html. Gum Disease: No Magic Bullet. Archive Sep. 15, 1998.

ThirdAge.com,http://www.thirdage.com/news/archive/980990–01.html,?rs. New Gel to Alter Gum Disease Treatment. Archive Sep. 9, 1998.

OralPharma, Inc. News Article. Warminster, Pa., Apr. 26, 2000 (PRNewswire). FDA Accepts OraPharma's New Drug Application for MPTS in Adult Periodontis.

American Dental Technologies, Inc. News Article. Corpus Christi, Texas, Apr. 25, 2000 (BW Health Wire). American Dental Technologies Announces Patent for Treating Periodontal Disease.

Atrix Laboratories, Ltd. News Article. London, Sep. 23, 1999 (PRNewswire). Atrix Announces Results for Expanded Utility of ATRIDOX Periodontal Therapy.

Donald E. and Delia B. Baxter Foundation & Lucille P. Markey Charitable Trust. News Article. Stanford, Calif (BW Health Wire) Dec. 6, 1999. New Analysis Reveals Human Mouth Carries More Germs Than Expected.

Realage.com, http://www.realage.com/About_RA/12ways.html. Top 12 ways to reduce your RealAge. Oct. 14, 1999.

American Academy of Periodontology. News Article. Chicago, Sep. 16, 1999 (PRNewswire). Periodontists Can Help Brides Achieve Gleaming Wedding Smiles.

Lordon.com,http://www.lordan.com/pages/category.htm. The Category. Aug. 29, 1999.

Journal of the American Dental Association. News Article. Starving Bacteria of Iron Might Prevent Periodontitis, say Researchers. JADA, vol. 124, p. 26. Aug., 1999.

Pollick M., Innovations in Toothpaste, Businesss Weekly, Herald–Tribune, Sarasota, Florida. May 31, 1999.

* cited by examiner

SYSTEM AND METHOD FOR APPLYING ORAL FLUID ABSORBING MATERIAL TO DENTAL ARCHES, WITH APPLICATION IN TREATMENT OF PERIODONTAL GUM DISEASE

This Application is a Continuation-In-Part of application Ser. No. 09/549,301 filed Apr. 13, 2000, (now U.S. Pat. No. 6,322,772), and further, via said 301 Application, this Application also Claims Benefit of Provisional Patent Application Ser. No. 60/145,028 filed Jul. 22, 1999.

TECHNICAL FIELD

The present invention relates to application of materials in mouths of subjects, and more specifically to a method of applying material(s) which absorb oral fluids to dental arches, which method finds particularly relevant application in the context of the of treatment periodontal gum disease.

BACKGROUND

Utility patent application Ser. No. 09/549,301 filed Apr. 13, 2000, and Provisional Patent Application Ser. No. 60/145,028 filed Jul. 22, 1999 are included hereinto by reference.

Typical approaches to applying dentifrice in liquid, powder, gel or paste form include toothbrush, flossing, rinsing and by use of pressure driven sprays. Less common, but known methods include use of self-sticking strips and impregnated finger cots.

Also known are teeth whitening agent delivery system "trays" which are of a shape to enable loose fit around teeth. In use a whitening agent is placed into said tray and the tray is then caused to be loosely positioned around a dental arch, such that the whitening agent is placed into direct contact with teeth for some period of time.

Further, in the treatment of periodontal gum disease it is known to apply antibiotics is via placement of antibiotic containing carrier means under the gum in contact with teeth.

A Patent Search was conducted. The results thereof are:

U.S. Pat. No. 4,344,931 to Aguilar which describes a dry powder incorporating psyllium husk fiber.

U.S. Pat. No. 4,812,308 to Winston et al., which describes sodium bicarbonate containing tooth paste.

U.S. Pat. No. 5,294,432 to Winston et al. which describes dentifrices incorporating alkali metal pyrophosphate salts and sodium bicarbonate in amounts effective to inhibit calculus formation on teeth.

U.S. Pat. No. 4,981,698 to Cherukuri et al. describes a multiple encapsulated sweetener delivery system and method of preparation in relation to psyllium.

U.S. Pat. No. 5,004,595 to Cherukuri et al. describes a psyllium delivery system.

U.S. Pat. No. 5,143,728 to Cappei et al. describes psyllium- containing compositions and methods.

U.S. Pat. No. 4,813,613 to Salete describes a process for obtention of high purity mucilage and mentions the use of sodium bicarbonate and psyllium fiber.

U.S. Pat. No. 3,339,547 to Drabkowski describes a topical arch tray for use in topical treatment of teeth and/or gums of a dental patient.

U.S. Pat. No. 3,527,219 to Greenburg describes an applicator for the treatment of teeth and/or gums with fluorides or other medications.

U.S. Pat. No. 3,844,286 to Cowen describes a resealable medicament dental carrier and method.

U.S. Pat. No. 5,323,787 to Pratt describes a custom fitted mouthpiece with medicated pad and container.

U.S. Pat. No. 5,575,645 to Fontenot illustrates an apparatus and method for whitening teeth.

U.S. Pat. No. 5,863,202 to Fontenot describes a system and method for treatment of dentition.

What was specifically not found is a non-invasive method of applying materials for absorbing oral fluids comprising providing a means for containing material for absorbing oral fluids and causing material which absorbs oral fluids to be contained within said means, said means for containing material for absorbing oral fluids being of an appropriate shape and size to loosely fit to at least one dental arch of said subject, such that, in use, material which absorbs oral fluid can be placed into contact with said at least one dental arch by positioning said means for containing material for absorbing oral fluids into loose contact with at least one dental arch of said subject. The present invention method then provides for positioning said means for containing material for absorbing oral fluids in loose contact with at least one dental arch of said subject such that material for absorbing oral fluids placed thereinto is placed into direct contact with at least one dental arch of said subject.

Even in view of the prior art, need remains for methodology for applying material for absorbing oral fluids to gums of subjects, particularly where said subjects present with periodontal gum disease.

SUMMARY OF THE INVENTION

It is therefore a purpose and/or objective of the present invention to teach a method of treating upper and/or lower dental arches of a subject, particularly where said subject has periodontal gum disease.

It is another purpose and/or objective of the present invention to teach a method of treating upper and/or lower dental arches of a subject, particularly where said subject has periodontal gum disease, which method is mediated by use of a means for containing material for absorbing oral fluids and causing material which absorbs oral fluids to be contained therewithin, such that in use placing said means for containing material for absorbing oral fluids into loose contact with at least one dental arch of said subject, causes said material for absorbing oral fluids to be placed into direct contact with at least one dental arch of said subject.

Other purposes and/or objectives of the present invention will become apparent by a reading of the Specification and the Claims.

DISCLOSURE OF THE INVENTION

The present invention is a method of treating upper and/or lower dental arches of an identified subject, particularly where said subject has periodontal gum disease. The method comprises providing a means for containing material for absorbing oral fluids and causing material which absorbs oral fluids to be contained therewithin, said means for containing material for absorbing oral fluids being of an appropriate shape and size to loosely fit to at least one dental arch of said subject. In use material which absorbs oral fluid is placed into contact with said at least one dental arch by positioning said means for containing material for absorbing oral fluids into loose contact with at least one dental arch of said subject, such that said material for absorbing oral fluids in placed into direct contact with at least one dental arch of said subject.

The material which absorbs oral fluids is typically selected to comprise potable water as a moistening agent, in combination with sodium bicarbonate and a material, (eg. psyllium husk fiber), which demonstrates absorbing and/or expanding properties, when placed into contact with oral fluids. The material which absorbs oral fluids can be selected to comprise at least one antimicrobial agent as well. When present, the antimicrobial agent(s) can be selected based upon results of analysis of the microbes present in a subject's gums as determined by performing an analysis of tissue obtained from said subject's mouth.

The material which absorbs oral fluids generally can be selected to comprise, in functional combination, at least two selections from the group consisting of:
   potable water as a moistening agent;
   sodium bicarbonate;
   psyllium husk fiber; and
   at least one antimicrobial agent.

While not critical, a nominal, non-limiting, time for which application of the material which absorbs oral fluids is nominally about seven minutes or more, and a flavoring can be added to make the application more pleasant.

The means for containing material for absorbing oral fluids can be generic or custom formed in conjunction with dental procedures such as used to mediate crown production. Further it can be single or double sided to treat one dental arch, or both upper and lower denatal arches simultaneously. Where the means for containing material for absorbing oral fluids is single sided, it is standard practice to then tend to upper and lower dental arches sequentially in either order. Further, the means for containing material for absorbing oral fluids can be, but need not be, made of a porous material.

An alternative approach requires that the material which absorbs oral fluid and which is suitable for being placed into contact with at least one dental arch of a subject can be by brushing and/or swabbing.

It is noted that the present invention can involve treating both upper and/or lower dental arches fo a subject simultaneously or in sequential order, with either the upper or lower being treated first.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A method of treating upper and/or lower dental arches of a subject comprising the steps of:
   a. identifying a subject, at least one dental arch selected from the group consisting of:
      upper; and
      lower;
   thereof is to be treated;
   b. providing a means for containing sodium-bicarbonate and/or psyllium husk fiber material for absorbing oral fluids and causing material which absorbs oral fluids to be contained therewithin, said means for containing material for absorbing oral fluids being of an appropriate shape and size to loosely fit to at least one dental arch of said subject, such that said material which absorbs oral fluid can be placed into contact with said at least one dental arch by positioning said means for containing material for absorbing oral fluids into loose contact with at least one dental arch of said subject;
   c. positioning said means for containing material for absorbing oral fluids, in loose contact with at least one dental arch of said subject such that said material for absorbing oral fluids in placed into direct contact with at least one dental arch of said subject.

2. A method of treating upper and/or lower dental arches as in claim 1, in which said material which absorbs oral fluids is selected to comprise at least one selection from the group consisting of:
   potable water as a moistening agent; and
   with optional flavoring.

3. A method of treating upper and/or lower dental arches as in claim 1, in which the material which absorbs oral fluids is selected to comprise sodium bicarbonate.

4. A method of treating upper and/or lower dental arches as in claim 3, in which the material which absorbs oral fluids is selected to further comprise a material which demonstrates absorbing and/or expanding properties, and optionally dental arch binding properties when placed into contact with oral fluids.

5. A method of treating upper and/or lower dental arches as in claim 4, in which the material which demonstrates absorbing and/or expanding properties, and optionally dental arch binding properties is selected to comprise psyllium husk fiber.

6. A method of treating upper and/or lower dental arches as in claim 1, in which the material which absorbs oral fluids is selected to comprise at least one antimicrobial agent.

7. A method of treating upper and/or lower dental arches as in claim 1, in which the material which absorbs oral fluids is selected to comprise an antimicrobial agent.

8. A method of treating upper and/or lower dental arches as in claim 1, in which said material which absorbs oral fluids to is caused to be contained therewithin, in caused to contact said at least one dental arch of said subject for a period of time of at least seven minutes.

9. A method of treating upper and/or lower dental arches as in claim 1, in which the material which absorbs oral fluids is selected to comprise, in functional combination, at least two selections from the group consisting of:
   potable water as a moistening agent;
   sodium bicarbonate;
   psyllium husk fiber;
   at least one antimicrobial agent.

10. A method of treating upper and/or lower dental arches as in claim 1, in which the material which absorbs oral fluids is selected to comprise a functional combination of:
   potable water as a moistening agent;
   sodium bicarbonate;
   psyllium husk fiber;
   at least one antimicrobial agent.

11. A method of treating upper and/or lower dental arches comprising the steps of:
   a. identifying a subject, at least one dental arch selected from the group consisting of:
      upper; and
      lower;
   thereof is to be treated;
   b. providing a material which absorbs oral fluid and which is suitable for being placed into contact with at least one dental arch of said subject by at least one means selected from the group consisting of:
      brushing; and
      swabbing;
   said material which absorbs oral fluid being comprised of at least two selections from the group consisting of:

bicarbonate of soda;

psyllium husk fiber; and at least one antimicrobial agent.

12. A method of treating upper and/or lower dental arches as in claim 11 in which the material which absorbs oral fluid is selected to be comprised of:

bicarbonate of soda;

psyllium husk fiber; and at least one antimicrobial agent;

in combination with a moistening agent.

13. A method of treating upper and/or lower dental arches as in claim 12 in which at least one selection is made from the group consisting of:

potable water is the moistening agent; and flavoring is included.

14. A method of treating periodontal gum disease in upper and/or lower dental arches of a subject comprising the steps of:

a. identifying a subject who presents with periodontal gum disease, in which subject at least one dental arch selected from the group consisting of:

upper; and lower;

thereof is to be treated;

b. providing a means for containing material for absorbing oral fluids and causing material which absorbs oral fluids to be contained therewithin, said means for containing material for absorbing oral fluids being of an appropriate shape and size to loosely fit to at least one dental arch of said subject, such that said material which absorbs oral fluid can be placed into contact with said at least one dental arch by positioning said means for containing material for absorbing oral fluids into loose contact with at least one dental arch of said subject;

c. positioning said means for containing material for absorbing oral fluids, in loose contact with at least one dental arch of said subject such that said material for absorbing oral fluids in placed into direct contact with at least one dental arch of said subject.

15. A method of treating periodontal gum disease in upper and/or lower dental arches of a subject as in claim 14, in which the material for absorbing oral fluids is comprised of at least two selections from the group consisting of:

bicarbonate of soda;

psyllium husk fiber; and at least one antimicrobial agent;

in combination with at least one selection made from the group consisting of:

potable water Is present as moistening agent; and flavoring.

16. A method of treating upper and/or lower dental arches of a subject as in claim 1, in which the upper and lower dental arches are treated one at a time, in either sequential.

17. A method of treating upper and/or lower dental arches of a subject as in claim 1, in which the upper and lower dental arches are treated one at a time, in either sequential, each for a nominal period or seven minutes.

18. A method of treating periodontal gum disease in upper and/or lower dental arches of a subject as in claim 14, in which the upper and lower dental arches are treated one at a time, in either sequential order.

19. A method of treating periodontal gum disease in upper and/or lower dental arches of a subject as in claim 14, in which the upper and lower dental arches are treated one at a time, in either sequential, each for a nominal period or seven minutes.

20. A method of treating periodontal gum disease in upper and/or lower dental arches of a subject as in claim 15, in which at least one antimicrobial agent is selected to be part of said material for absorbing oral fluids, and wherein said at least one antimicrobial agent is selected based upon performing an analysis of tissue obtained from said subject's mouth.

21. A method of treating upper and/or lower dental arches as in claim 1, in which the material which absorbs oral fluids is selected to comprise psyllium husk fiber.

22. A means for containing material for absorbing oral fluids with sodium bicarbonate and/or psyllin husk fiber material which absorbs oral fluids contained therewithin, said means for containing material for absorbing oral fluids being of an appropriate shape and size to loosely fit to at least one dental arch of said subject, such that said material which absorbs oral fluid can be placed into contact with said at least one dental arch by positioning said means for containing material for absorbing oral fluids into loose contact with at least one dental arch of said subject;

such that in use said means for containing material for absorbing oral fluids is caused to be in loose contact with at least one dental arch of said subject such that said material for absorbing oral fluids is placed into direct contact with at least one dental arch of said subject.

23. A means for containing material for absorbing oral fluids with material which absorbs oral fluids contained therewithin as in claim 22, in which the material which absorbs oral fluids comprises at least two selections from the group consisting of:

potable water as a moistening agent;

sodium bicarbonate;

psyllium husk fiber;

at least one antimicrobial agent.

24. A means for containing material for absorbing oral fluids with material which absorbs oral fluids contained therewithin as in claim 22, in which the material which absorbs oral fluids comprises sodium bicarbonate.

25. A means for containing material for absorbing oral fluids with material which absorbs oral fluids contained therewithin as in claim 22, in which the material which absorbs oral fluids comprises psyllium husk fiber.

* * * * *